US 8,316,985 B2

(12) United States Patent
Bain et al.

(10) Patent No.: US 8,316,985 B2
(45) Date of Patent: Nov. 27, 2012

(54) METHODS AND DEVICES FOR SOUND ABATEMENT OF AN ABDOMINAL STOMA

(76) Inventors: Mark Bain, Shelby Township, MI (US); Andrea Bain, Shelby Township, MI (US)

(*) Notice: Subject to any disclaimer, the term of this patent is extended or adjusted under 35 U.S.C. 154(b) by 0 days.

(21) Appl. No.: 12/977,029

(22) Filed: Dec. 22, 2010

(65) Prior Publication Data

US 2011/0147114 A1 Jun. 23, 2011

Related U.S. Application Data

(60) Provisional application No. 61/289,997, filed on Dec. 23, 2009, provisional application No. 61/356,198, filed on Jun. 18, 2010, provisional application No. 61/377,584, filed on Aug. 27, 2010, provisional application No. 61/377,590, filed on Aug. 27, 2010.

(51) Int. Cl.
*A47B 81/06* (2006.01)
*A61F 2/02* (2006.01)
*A61F 5/44* (2006.01)
*G10K 11/16* (2006.01)

(52) U.S. Cl. .......... 181/198; 181/296; 600/32; 604/332; 604/333; 604/337; 604/338; 604/339; 604/343; 604/344; 604/345

(58) Field of Classification Search .......... 181/198, 181/296; 604/332, 333, 337, 338, 339, 343, 604/344, 345
See application file for complete search history.

(56) References Cited

U.S. PATENT DOCUMENTS

| | | | | |
|---|---|---|---|---|
| 2,759,477 A | * | 8/1956 | Mains | 604/343 |
| 2,910,065 A | * | 10/1959 | Marsan | 604/344 |
| 3,302,647 A | * | 2/1967 | Marsan | 604/336 |
| 3,447,533 A | * | 6/1969 | Spicer | 600/32 |
| 4,294,252 A | * | 10/1981 | Einset | 604/345 |
| 4,406,657 A | * | 9/1983 | Curutcharry | 604/328 |

(Continued)

FOREIGN PATENT DOCUMENTS

CA 2319222 A1 8/2002
(Continued)

OTHER PUBLICATIONS

PCT International Search Report and Written Opinion for PCT/US2010/062058, to Bain et al., 11 pages, Sep. 19, 2011.
(Continued)

*Primary Examiner* — David Warren
*Assistant Examiner* — Christina Russell
(74) *Attorney, Agent, or Firm* — McPherson IP Law Office, PLLC (57) ABSTRACT

The present invention provides methods and devices for the abatement of noise emanating from surgically created abdominal stomas. In one embodiment, the present invention provides a sound abatement device for an abdominal stoma. The device includes a noise suppressor formed of sound dampening material, which defines an opening and cavity suitable in size and shape for receiving and enveloping a stoma formed through a body wall of an individual. The device further includes a support arm extending from the noise suppressor, which includes a first end connected to the noise suppressor and a second end disposed opposite thereof. The device further includes a base member disposed proximate the second end of the support arm, which includes an attachment for connection to an individual. The device also includes an attachment feature for releasable attachment of the second end of the support arm to the base.

20 Claims, 9 Drawing Sheets

U.S. PATENT DOCUMENTS

| | | | | |
|---|---|---|---|---|
| 4,592,750 | A | * | 6/1986 | Kay ............................ 604/337 |
| 4,596,566 | A | * | 6/1986 | Kay ............................ 604/343 |
| 4,636,205 | A | * | 1/1987 | Steer ........................... 604/338 |
| 4,636,206 | A | * | 1/1987 | Ederati et al. ................ 604/340 |
| 4,929,245 | A | * | 5/1990 | Holtermann et al. ......... 604/338 |
| 4,941,869 | A | * | 7/1990 | D'Amico ....................... 600/32 |
| 5,178,614 | A | * | 1/1993 | McDowell et al. ........... 604/332 |
| 5,207,652 | A | * | 5/1993 | Kay ............................ 604/180 |
| 5,248,308 | A | * | 9/1993 | von Emster ................... 604/337 |
| 5,338,315 | A | * | 8/1994 | Baker ........................... 604/345 |
| 5,607,412 | A | * | 3/1997 | Brown .......................... 604/332 |
| 5,626,570 | A | * | 5/1997 | Gallo ............................ 604/345 |
| 5,653,701 | A | * | 8/1997 | Millman ....................... 604/345 |
| 5,865,820 | A | * | 2/1999 | Myello et al. ................. 604/345 |
| 5,947,941 | A | * | 9/1999 | Leise et al. ................... 604/338 |
| 6,050,983 | A | * | 4/2000 | Moore et al. ................. 604/333 |
| 6,129,715 | A | * | 10/2000 | Cunningham ............... 604/332 |
| 6,257,240 | B1 | | 7/2001 | Shesol ......................... 128/877 |
| 6,328,721 | B1 | * | 12/2001 | Prohaska ..................... 604/338 |
| 6,485,476 | B1 | * | 11/2002 | von Dyck et al. ............ 604/332 |
| 6,576,808 | B1 | | 6/2003 | Dreyer .......................... 602/42 |
| 6,689,111 | B2 | * | 2/2004 | Mulhauser et al. ........... 604/332 |
| 6,723,079 | B2 | | 4/2004 | Cline ........................... 604/337 |
| 7,166,091 | B1 | * | 1/2007 | Zeltner ......................... 604/345 |
| 7,258,661 | B2 | * | 8/2007 | Davies et al. .................. 600/32 |
| 7,270,860 | B2 | | 9/2007 | Giori ............................ 428/35.7 |
| 7,347,844 | B2 | * | 3/2008 | Cline et al. ................... 604/337 |
| 7,559,922 | B2 | * | 7/2009 | Botten .......................... 604/333 |
| 7,604,622 | B2 | * | 10/2009 | Pedersen et al. ............. 604/333 |
| 2004/0171999 | A1 | * | 9/2004 | Andersen et al. ............. 604/332 |
| 2005/0107758 | A1 | * | 5/2005 | Hogan et al. ................. 604/327 |
| 2007/0005033 | A1 | * | 1/2007 | Ciok et al. .................... 604/344 |
| 2010/0174256 | A1 | * | 7/2010 | Rosengren .................... 604/344 |
| 2012/0010580 | A1 | * | 1/2012 | Forbes et al. ................. 604/339 |

FOREIGN PATENT DOCUMENTS

| | | | |
|---|---|---|---|
| DE | 202010004472 | * | 9/2010 |
| EP | 2002811 A1 | | 6/2007 |
| WO | WO 87/06823 A1 | | 11/1987 |
| WO | WO 97/16141 A1 | | 5/1997 |

OTHER PUBLICATIONS

Website 1: https://www.kachi-do.com/budonordekfsuperfemalechestguard-p-1565.html, printed Nov. 16, 2009, 4 pages.

Website 2: http://images.google.com/imgres?imgurl=http://www.ostomart.co.uk/Fireworks%2520Graphics/s..., printed Nov. 2, 2009, 1 page.

Website 3: http://homepage.ntlworld.com/jmwest/small/Dscf0058.jpg, printed Nov. 4, 2009, 1 page.

Website 4: http://homepage.ntlworld.com/jmwest/small/Dscf0057.jpg, printed Nov. 4, 2009, 1 page.

Website 5: http://pk-fashions.com/New/images/5StepsNEW.JPG, printed Nov. 2, 2009, 1 page.

Website 6: http://images.allegrocentral.com/09/AB/Dry-Pro-Waterproof-Ostomy-Cover-555611-PRODUCT..., printed Nov. 4, 2009, 1 page.

Website 7: http://images.google.com/imgres?imgurl=http://www.celebrationostomysupportbelt.com/images/..., printed Nov. 4, 2009, 1 page.

Website 8: http://quietpouch.com/, printed Nov. 3, 2009, 1 page.

* cited by examiner

Fig-21

METHODS AND DEVICES FOR SOUND ABATEMENT OF AN ABDOMINAL STOMA

CROSS-REFERENCE TO RELATED APPLICATION

The present application claims benefit of U.S. Provisional Patent Application No. 61/289,997, filed Dec. 23, 2009, U.S. Provisional Patent Application No. 61/356,198, filed Jun. 18, 2010, U.S. Provisional Patent Application No. 61/377,584, filed Aug. 27, 2010, and U.S. Provisional Patent Application No. 61/377,590, filed Aug. 27, 2010, the contents of which are hereby incorporated by reference in their entirety for all purposes.

FIELD OF THE INVENTION

The present invention relates to methods and devices for reducing sounds emanating from a surgically created abdominal stoma due to the expulsion of gas, excrement or otherwise.

BACKGROUND

Certain diseases of the bowel involve removing a portion of the intestine. This can create a need for an alternate path for the discharge of bodily excrement, i.e. fecal waste. This surgical procedure is called an ostomy and a person having undergone this procedure is medically referred to as an ostomate. Common types of ostomies include colonostomies and ileostomies. An ostomy involves the formation of an opening through an abdomen wall. A portion of the bowel is then pulled through the abdominal wall and an incision is made through the bowel to allow excrement to exit. The surrounding bowel is then sutured or otherwise attached to an exterior portion of the abdominal, which creates what is commonly referred to as a stoma. An ostomate will utilize an appliance such as a colonostomy bag or otherwise, which is attached to the individual's skin, directly about the stoma, and is periodically emptied, as required.

Ostomates are often faced with a permanent and life changing condition affecting many personal issues such as diet, dressing/wardrobe, and bathroom habits. Ostomates learn to modify their lifestyle to accommodate the intricacies of having a stoma, including learning the use of various new hardware, care and maintenance of the stoma, and other challenges. Issues such as rejoining the workplace or social circles can be particularly worrisome for a new ostomate, as much anxiety is created based upon the uncertainties and new personal challenges that go along with having a stoma.

One particular social drawback for an ostomate is dealing with intestinal gas, i.e. flatulence. Prior to the ostomy, the individual could control the release of flatulence through the sphincter muscle. However, an ostomate no longer has this control, since the flatulence and excrement now freely pass through the stoma, which has no muscles. For many ostomates, it is difficult to control the resulting sounds, which can be embarrassing. As such, new ostomates begin to identify trends of higher stoma activity, or inactivity, based on factors such as time of day, meal consumption, diet or even menstrual cycles in order to better predict potential stoma activity.

All too often, flatulence, or excrement, and resultant sounds, will have a tendency to pass at the most inopportune time, such as during a meeting or a social event. In these circumstances, the ostomate will have little or no warning to the impending sound. Due to the social stigma associated with flatulent noise, and given the personal nature of having an ostomy, many new ostomates find the betraying sounds of passing flatulence and excrement particularly embarrassing. This can be especially true when the new ostomate rejoins the workforce or social circles, as he or she is continuously self-conscious about the potential noise and preemptive action needed to hide their personal condition.

While there have been developments in managing other challenges such as odor discharging from a stoma, little has been effectively done to control noise emanating from the stoma. One sound abatement device that has been developed comprises a woven pouch configured to receive a stoma bag. However, the pouch requires the use of additional hardware, such as a belt or otherwise, to maintain the position of the bag. Unfortunately, the use of additional hardware can be noticeable and uncomfortable as the material of the hardware is typically kept under pressure. During the day, it is difficult for an individual to obtain reprieve from irritation caused by the additional hardware and must wait until he or she is in private, such as at home, to remove the hardware. This is because, often, the device is bulky and wrapped entirely about the individual and disposed under clothing. Further, some bags used for sound abatement is formed of woven material, which is less than satisfactory for the reduction of noise.

In view of the foregoing, there is a need for improved methods and devices for providing noise abatement for an ostomate's stoma, particularly methods and devices that are discreet, are easily operable and removable, and provide an effective level of confidence for the individual.

SUMMARY OF THE INVENTION

The present invention provides methods and devices for the abatement of noise emanating from surgically created abdominal stomas. In one aspect, the present invention provides a device capable of sealing the stoma from a surrounding area of the individual and in one particular configuration is formed of a material particularly suited for sound attenuation. In another aspect, the present invention provides a sound attenuating device that extends over only a portion of the individual and in one particular configuration is easily removable. In still another aspect, the present invention provides a sound attenuating device that is moveable with respect to the stoma to provide controlled sealing of the stoma from a surrounding area of the individual while still maintaining free flow of excrement and/or gas into a corresponding stoma bag. It should be appreciated, as shown in described herein, that other advantageous aspects of the present invention exist.

In view of the foregoing, in one exemplary embodiment the present invention provides a sound abatement device for an abdominal stoma. The device includes a noise suppressor formed of sound dampening material. The noise suppressor defines an opening and cavity suitable in size and shape for receiving and enveloping a stoma formed through a body wall of an individual. The device further includes a support arm extending from the noise suppressor, the support arm includes a first end connected to the noise suppressor and a second end disposed opposite thereof. The device further includes a base member disposed proximate the second end of the support arm, the base member includes an attachment for connection to an individual. The device also includes an attachment feature for releasable attachment of the second end of the support arm to the base, wherein upon engagement the noise suppressor is cantilevered from the base.

In another exemplary embodiment, the present invention provides a sound abatement device for an abdominal stoma. The device includes a noise suppressor formed of sound dampening material. The noise suppressor includes: i) a cup defining an opening and cavity suitable in size and shape for receiving and enveloping a stoma formed through a body wall of an individual, and ii) a support arm integrally formed and extending away from the cup, wherein the noise suppressor defines a seal formed about the cavity configured to engage a body wall of an individual. The device further includes a base member disposed proximate an end of the support arm opposite the cup. The base member includes a first side having an attachment for connection to a body wall of an individual and a second side configured for connection to the noise suppressor. The device also includes an attachment feature for releasable attachment of the second end of the support arm to the second side of the base member, wherein upon attachment of the support arm to the base member the noise suppressor is cantilevered form the base member and is moveable from a first position and a second position.

In another exemplary embodiment, the present invention provides a method of providing noise abatement for a surgically created abdominal stoma. The method includes the step of pivotally mounting a noise suppressor to an individual. The noise suppressor is moveable between a first position and a second position, wherein in the first position the noise suppressor envelops a stoma and substantially seals the stoma from a surrounding area of the individual, and wherein in a second position the noise suppressor is spaced from the individual.

In another exemplary embodiment, the present invention provides a method of providing noise abatement for a surgically created abdominal stoma. The method includes the step of disposing a noise suppressor adjacent a stoma of an individual. The noise suppressor defines an opening and a cavity for receiving and enveloping the stoma. The noise suppressor further includes an annular portion formed about the opening for creating a seal when pressed against a corresponding member. The method further includes fixedly attaching the noise suppressor to a base member, the base member being adhesively attached to an exterior body wall of an individual to allow the noise suppressor to move between a first position and a second position. In the first position, the noise suppressor is supported by the base member and is displaced with respect to the individual to allow the noise suppressor to move with respect to the stoma. In a second position, the noise suppressor is pressed against the individual to envelope the stoma and form a seal about the cavity to seal the stoma from a surrounding area of the individual.

In another exemplary embodiment, the present invention provides an ostomy bag. The ostomy bag includes a bag having a first side and a second side. The first side of the bag defines an opening for receiving material expelled from a stoma. The ostomy bag further includes a sound abatement device disposed proximate the second side of the bag adjacent the opening. The sound abatement device is moveable with respect to the opening to envelope the stoma and cause sound abatement thereto.

In yet another exemplary embodiment, the present invention provides an ostomy device for the collection of waste emitted from a stoma. The ostomy device includes an ostomy bag having a first side and a second side. The first side of the ostomy bag defines an opening for receiving material expelled from a stoma. The ostomy device also includes a mount for connection of the ostomy bag to an individual. The mount includes an annular ring for attachment of the mount to the individual and a projecting member for attachment of the mount to the ostomy bag. The ostomy device also includes a sound suppressor disposed adjacent the second side of the ostomy bag. The ostomy device further includes a connector for attachment of the sound suppressor to the mount, wherein the sound suppressor is moveable with respect to the mount to envelope the stoma and cause sound abatement thereto.

The above-described and other features and advantages of the present invention will be appreciated and understood by those skilled in the art from the following detailed description, drawings, and appended claims.

BRIEF DESCRIPTION OF THE DRAWINGS

Other objects, features, advantages and details of the present invention appear, by way of example only, in the following detailed description of exemplary embodiments of the present invention, the detailed description referring to the drawings in which.

DESCRIPTION OF THE PREFERRED EMBODIMENTS

In general, the present invention relates to methods and devices for the attenuation of noise emanating from a surgically created abdominal stoma, particularly stomas formed from ostomies such as colonostomies and ileostomies. The present invention provides a noise attenuation device that is relative small, compact and low profile, as compared to prior systems. The noise attenuation device is also easy to use and can be installed or removed with a single hand. Further, the noise attenuation device reduces the amount of irritation and discomfort an individual must endure, particularly in public settings. Still further, the noise attenuation device gives the user a higher level of confidence in public settings as the device eliminates or drastically reduces stoma noises and is discrete.

Figure 1:
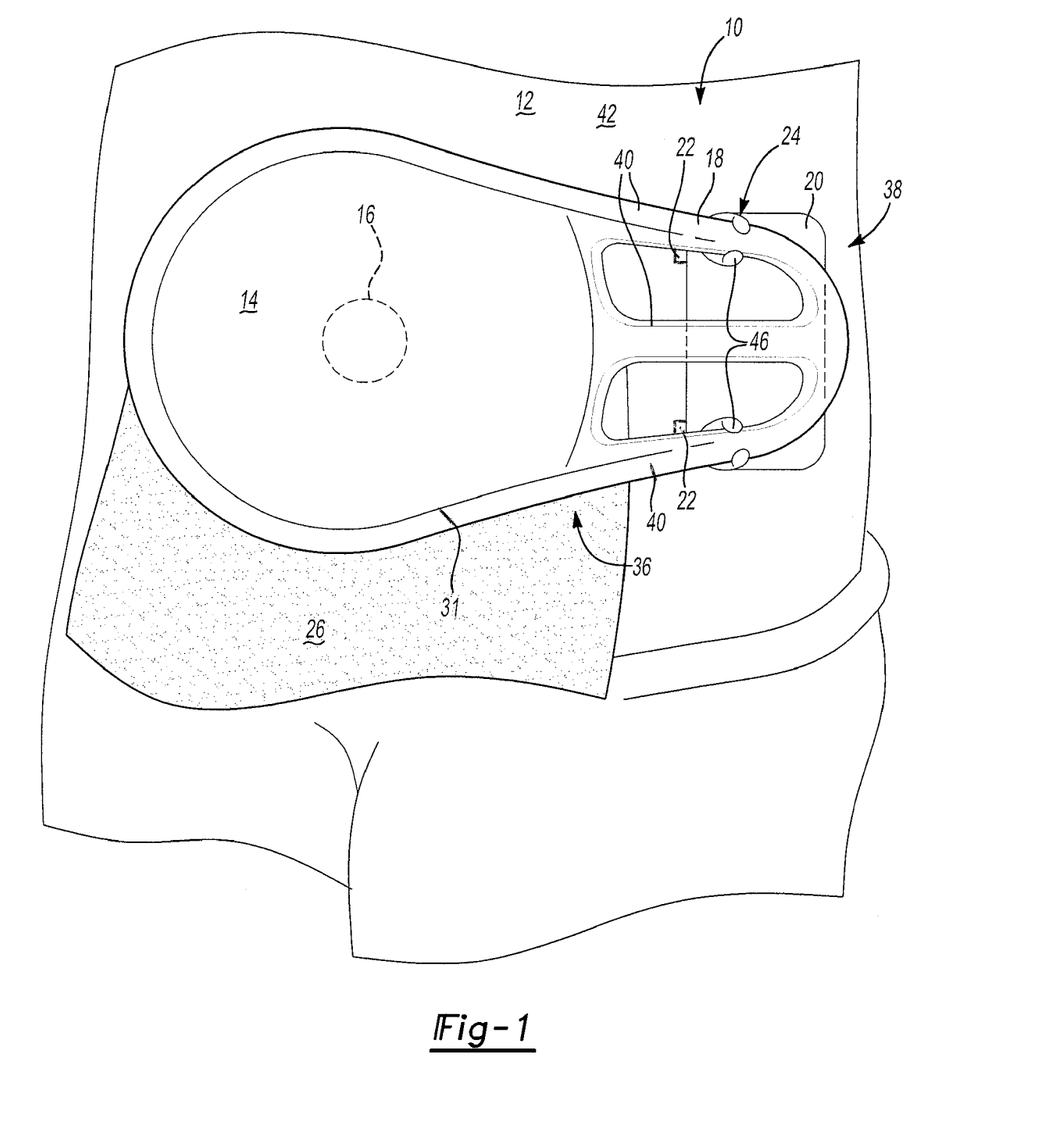
FIG. 1 illustrates a perspective view of an exemplary noise abatement device attached to an individual according to the teachings of the present invention.
Figure 2:
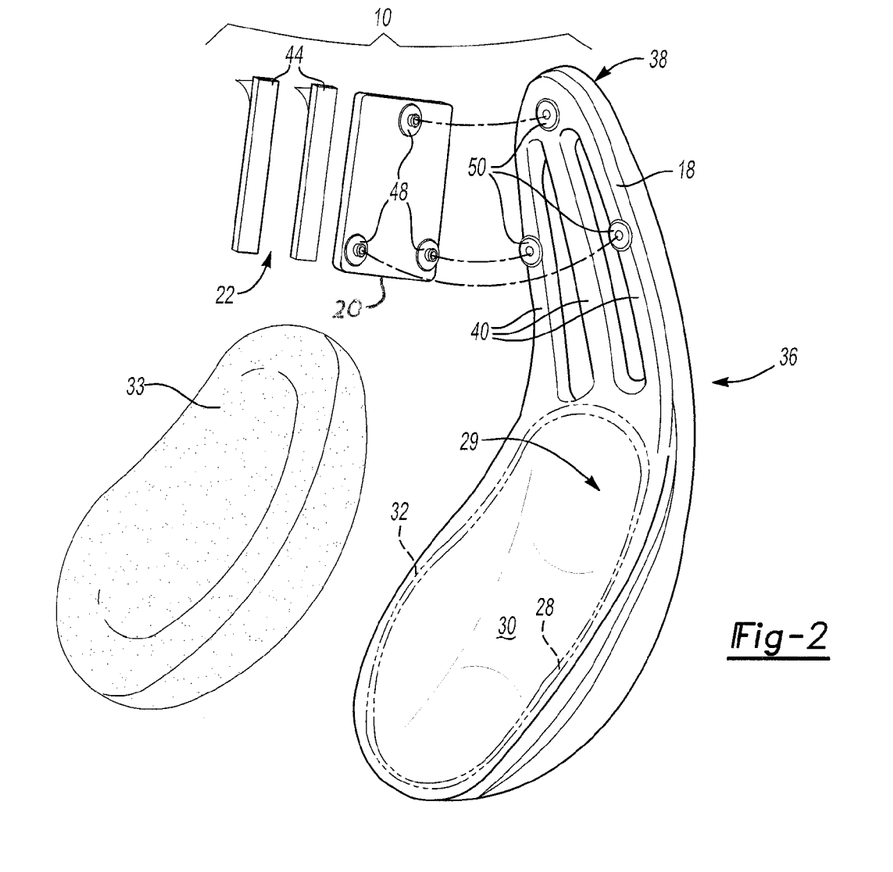
FIG. 2 illustrates an exploded perspective view of the noise abatement device shown in FIG. 1.
Figure 3:
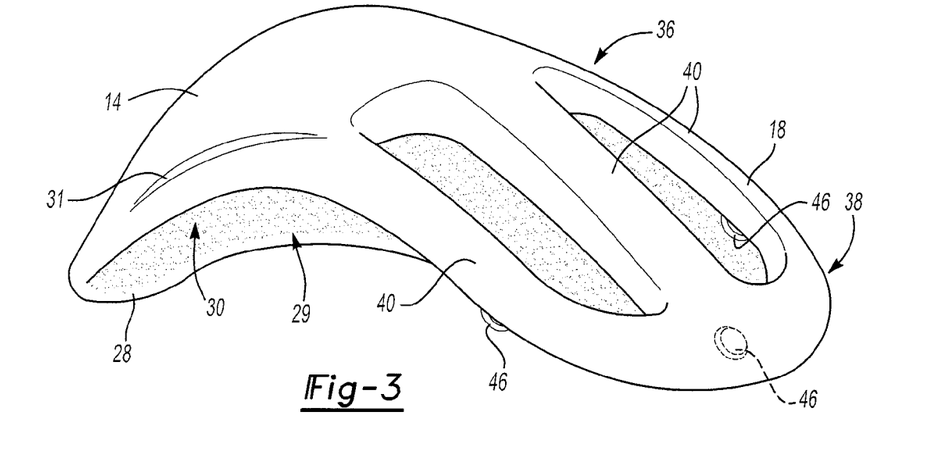
FIG. 3 illustrates a perspective view of the noise suppressor and support arm of the noise abatement device shown in FIG. 1.

Referring to FIGS. 1 through 3, an exemplary embodiment of a noise abatement device 10 for a stoma is shown attached to an individual 12. The device 10 includes a noise suppressor 14, disposed proximate a stoma 16, configured for providing sound dampening thereto. The device 10 further includes a support arm 18, extending from the noise suppressor 14, for providing cantilevered support of the noise suppressor 14. The noise suppressor 14 is further supported by and attached to the individual 12, via support arm 18, through a base 20. In one exemplary embodiment, the base 20 is attached to the individual through an epidermis attachment feature 22, though the base may also be indirectly attached to the individual. The device further includes a releasable attachment feature 24 for attachment of the noise suppressor 14 to the base 20.

Figure 4:
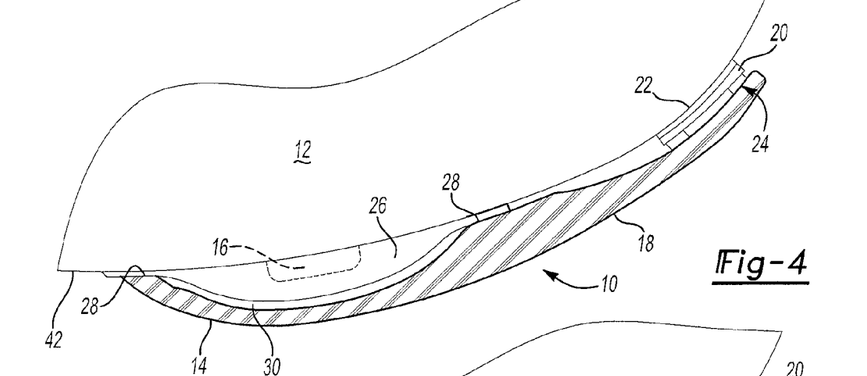
FIG. 4 illustrates a top partial cross-sectional view of an exemplary noise abatement device in a first position according to the teachings of the present invention.
Figure 5:
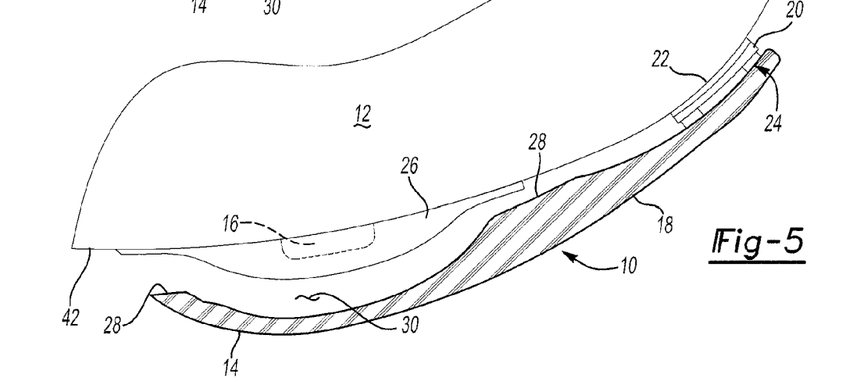
FIG. 5 illustrates a top partial cross-sectional view of an exemplary noise abatement device in a second position according to the teachings of the present invention.

In operation, referring to FIGS. 4 and 5, the noise abatement device 10 is configured for movement between a first position, shown in FIG. 4, and a second position, shown in FIG. 5. In the first position, the noise suppressor 14 substantially surrounds and envelopes the stoma 16 for sealing the stoma from a surrounding area of the individual 12. In the second position, the noise suppressor 14 is displaced with respect to the individual 12 to allow the noise suppressor 14 to move with respect to the stoma 16 and/or a stoma bag 26. Advantageously, the displacement of the noise suppressor 14 with respect to the individual allows free flow of excrement from the stoma 16 into the stoma bag 26. Further, in contrast to top mounted guards or other configurations completely wrapped about the individual 12, this spatial relationship, under certain circumstances, allows a user to freely or unobstructively view the ostomy hardware, e.g. ostomy bag or otherwise, because of a gap formed between the noise abatement device 10 and individual 12. Accordingly, in this configuration only the base 20 of the noise abatement device 10 is contacting the individual 12, which substantially reduces irritation commonly encountered with ostomy hardware. When the noise abatement device 10 is no longer needed or desired the noise suppressor 14 may be removed from the base 20.

In greater detail, referring to FIGS. 2 and 3, the noise suppressor 14 is suitable in size and shape for receiving a stoma 16. In one exemplary embodiment, the noise suppressor 14 includes an annular portion 28 defining an opening 29 leading to a cavity 30 formed by the noise suppressor 14, which forms a concave member. In one exemplary embodiment, the annular portion 28 extends entirely about the cavity 30. The annular portion 28 and cavity 30 are suitable in size and shape for receiving the stoma 16. In one exemplary embodiment, the annular portion 28 and cavity are suitable in size and shape for receiving other components commonly encountered with a stoma or stoma bag 26, such as an odor removal device or otherwise.

In one exemplary embodiment, the noise suppressor 14 includes additional features for providing further sound suppression. In one configuration, the noise suppressor 14 includes a contoured interior surface, such as cones, pyramids, spheres or otherwise, for suppressing sounds emanating from a stoma. The contoured interior surface may be molded with the material forming the noise suppressor 14 or may comprise a separate component. In another configuration, the noise suppressor 14 includes an interior surface formed of a sound deadening material, such as materials used to form an anechoic chamber, e.g. noise proof room, or otherwise. In another exemplary embodiment, referring to FIG. 2, the noise suppressor 14 includes an insert 33 configured for providing additional sound attenuation. The insert 33 may also be used for providing cushion to the stoma 16. The insert 33 may comprise a sponge-like material, other soft, flexible and/or pliable material and/or any of the materials described herein for forming the noise suppressor.

In one exemplary embodiment, the annular portion 28 is particularly shaped to follow the contours of an individual. For example, all or a portion of the annular portion 28 may be arcuate along one or more axes. In one exemplary embodiment, the annular portion 28 may comprise a material configured for forming a substantial seal. Also, it is contemplated that the annular portion 28 may be pliable and resilient (e.g. flexible) to form about an individual upon application of pressure and maintain a seal. To this end, it is contemplated that the noise suppressor 14 may include one or more grooves 31 for facilitating flexibility of the annular portion 28, though the material may be suitably flexible to form a seal without grooves 31. In another exemplary embodiment, it is contemplated that the annular portion 28 includes a seal member 32 extending annularly about the cavity 30. The seal member 32 may comprise any suitable sealant member, including any of the materials suitable for forming the noise suppressor 14, as described herein or otherwise. As such, it is also contemplated that the seal member 32 may also be pliable and resilient. Examples of suitable seal members 32 includes foam seals and rubber seals.

The noise suppressor 14 may be formed of any suitable material. In one preferred embodiment, the noise suppressor is formed of a material that is sound stifling to provide noise abatement. Examples of suitable materials include plastic, rubber, metal, combinations thereof or otherwise. In one particular exemplary embodiment, the material forming the noise suppressor is foam and more particularly closed-cell foam. Closed-cell foam is particularly advantageous for providing a light-weight semi-rigid structure that is both flexible, and capable of providing substantial sound stifling. Exemplary closed-cell foams that are suitable for forming the noise suppressor 14 of the present invention include polyurethane reaction injection foam or otherwise. Also, it is contemplated that the noise suppressor may be formed of more than one material to form a composite or include stiffening or other members.

The support arm 18 extends from the noise suppressor 14 and is configured to provide cantilevered support of the noise suppressor 14 in the first position, second position and during movement. The support arm 18 includes a first end 36 proximate the noise suppressor 14 and a second end 38 opposite thereof. In one exemplary embodiment, the support arm 18 is integrally formed with the noise suppressor 14 to form a unitary structure. Accordingly, it is contemplated that the support arm 18 may be formed of any of the suitable materials forming the noise suppressor 14 or otherwise.

The support arm 18 may be formed of any suitable shape for providing support for the noise suppressor 14. For example, as shown in the drawings, the support arm may comprise one or more, or plurality, of support members 40, that are joined at one or both ends of the support arm 18. Such support members 40 may include a particular cross-section to obtain desired flexibility. In one exemplary embodiment, as with the noise suppressor 14, the support arm 18 is shaped to generally correspond to a body wall member 42, e.g. abdomen or otherwise, of the individual 12 for maintaining a low profile of the device.

The base 20 is configured for attachment of the noise suppressor 14 to an individual 12. The base 20 may include any suitable size or shape for attachment of the noise suppressor 14 to an individual 12. In one exemplary embodiment, the base 20 comprises a substantially flat member. However, in another exemplary embodiment the base 20 is arcuate to extend along the body wall 42 of an individual 12.

In one exemplary embodiment, the base 20 is attached to the individual 12 using the epidermis attachment feature 22. In one preferred configuration, the epidermis attachment feature 22 is configured to maintain the base 20 substantially flush against the individual 12. The epidermis attachment feature 22 may comprise one or more individual attachment means extending over a surface area of the base 20. It is also contemplated that the attachment means may be sized to substantially cover a surface of the base adjacent the individual. In one exemplary embodiment, the attachment means comprises medical attachment means such as two-sided adhesive tape 44. However, it should be appreciated that other attachment means may be used including other adhesive means or otherwise.

In another exemplary embodiment, the base 20 is configured for attachment to another component, such as belt or otherwise configured for further attachment to an individual. This is particularly useful when an individual is using a belt or other component to support or mount an ostomy appliance, e.g. ostomy bag or otherwise. In such configurations, the base is attached to the belt or other component using any suitable attachment means such as mechanical attachment means (e.g. clips, fasteners, snap-fittings or otherwise), adhesives, sewing material, or otherwise. Still further, the base may be incorporated with the belt, or the belt may include the attachment features of the base for attachment of the noise suppressor 14 to the belt. Other configurations are possible.

Referring to FIGS. 2 and 6 through 11, several embodiments of the releasable attachment feature 24 of the present invention are shown. In contrast to prior systems, the releasable attachment feature 24 provides the ability to easily remove the noise suppressor 14 when not needed, such as at home, in a vehicle or other private setting. This reduces or eliminates the amount of discomfort or irritation the individual must endure. Further, the configurations of the releasable attachment feature 24 provide for easy installment and removal of the noise suppressor 14 as it can be removed or installed with a single hand. The releasable attachment feature 24 is configured for attachment of the noise suppressor 14 to the individual 12, via the base 20. The releasable attachment feature 24 may include a single attachment member or a plurality of attachment members or other attachment means. In one exemplary embodiment, each attachment member includes corresponding attachment members for engagement with one another.

In one embodiment, referring to FIG. 2, a plurality of attachment members 46 are provided. The plurality of attachment members 46 comprise magnetic connectors, wherein the second end 38 of the support arm 18 and the base 20 include a plurality of oppositely charged magnetic attachment members 46. In this configuration, the magnetic attachment members 46 comprise magnetic buttons wherein a first magnetic attachment member 48 includes an extension and a second magnetic member 50 includes an opening for receiving the extension to maintain alignment of the first magnetic member 48 with respect to the second magnetic member 50. However, it should be appreciated that other releasable attachment features 24 are possible, which may be used with any of the embodiments herein. For example, other contemplated releasable attachment members 24 include hook and latch, snap-fitting, threaded fasteners or other fastening means.

Figure 6:
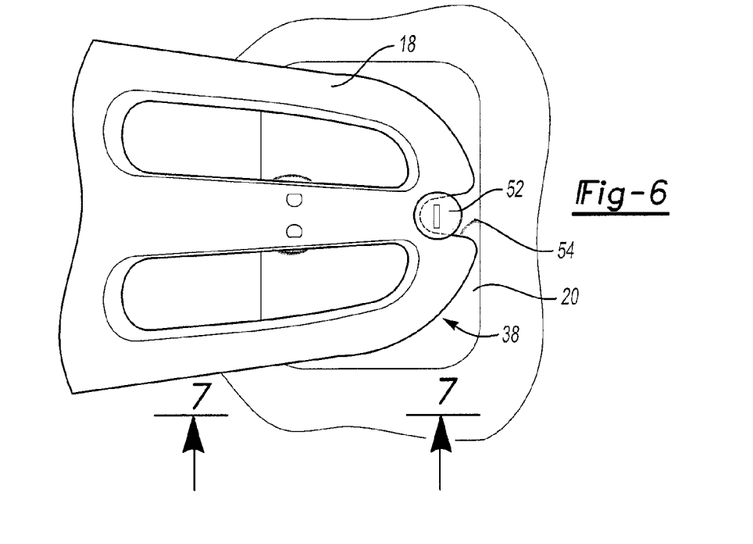
FIG. 6 illustrates a side elevational view of an exemplary attachment feature according to the teachings of the present invention.
Figure 7:
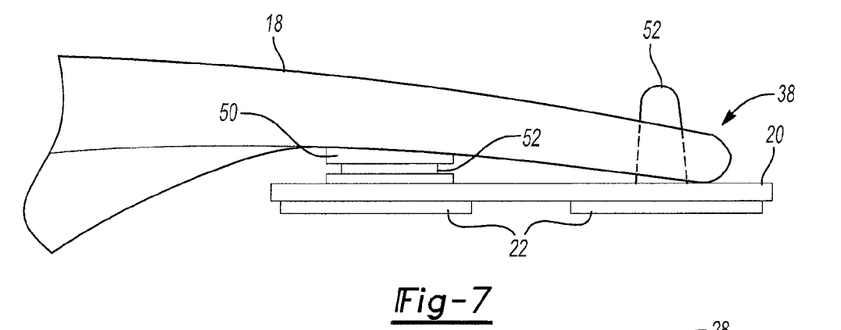
FIG. 7 illustrates a top elevational view of the attachment feature shown in FIG. 6.

In another embodiment, referring to FIG. 6, a noise abatement device 10 is providing having a releasable attachment feature 24 that includes a single set of oppositely charged magnetic attachment members 46. The releasable attachment feature 24 further includes an alignment guide 52 for substantially limiting rotational movement of the noise suppressor 14 and support arm 18, with respect to the base, about the releasable attachment feature 24. The alignment guide 52 engages a slot 54 formed at the second end 38 of the support arm 18 to limit lateral movement of the support arm 18.

Figure 8:
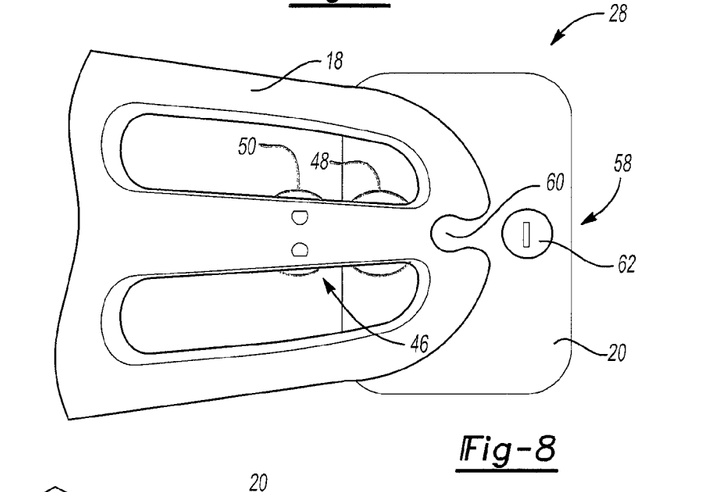
FIG. 8 illustrates a side elevational view of another exemplary attachment feature according to the teachings of the present invention.

In another embodiment, referring to FIG. 8, a noise abatement devise 10 is provided including a releasable attachment feature 24 that has a snap-fitting 58 configured for providing alignment and engagement between the support arm 18 and base 20. The snap-fitting 58 is formed by an opening 60 formed through the second end 38 of the support arm 18 that is configured for engagement with an extension 62 of the base 20. In one configuration, the support arm 18 forming the opening, the extension 62 or both are resiliently deformable to provide locking engagement upon insertion of the extension 62 into the opening 60. The releasable attachment feature further includes a set of oppositely charged magnetic attachment members 46, including corresponding extensions and openings, for maintaining engagement between the support arm 18 and base 20. In this configuration, during engagement between the support arm 18 and base 20, the snap-fitting 58 aligns the support arm 18 with the base and further locks the support arm 18 to the base. The magnetic attachment members provide further attachment of the support arm 18 to the base 20 and also limits or prevents rotational movement of the support arm about the extension 62. As with other embodiments, the noise suppressor 14, attached via support arm 18, is allowed to rotate between a first position and second position with respect to the base 20.

Figure 9:
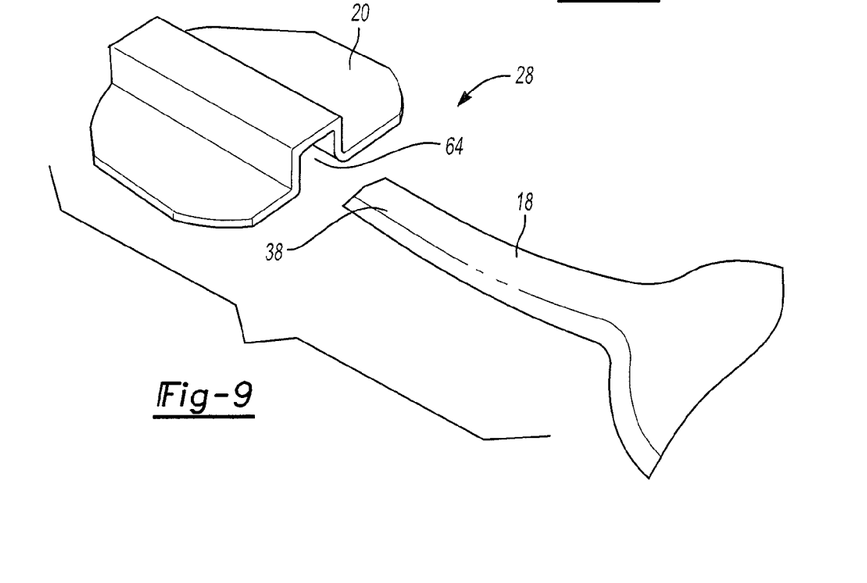
FIG. 9 illustrates a partially exploded perspective view of another exemplary attachment feature according to the teachings of the present invention.

In another exemplary embodiment, referring to FIG. 9, a noise abatement device 10 is provided including an attachment feature 24 that has a releasable friction fit configured for alignment and attachment between the support arm 18 and base 20. In this configuration, the base 20 includes an opening 64 configured for receiving the second end 38 of the support arm 18. In one configuration the second end 38 of the support arm 18 has an exterior cross-sectional shape corresponding to an interior cross-sectional shape of the opening 64. The cross-sectional shape of the second end 38 and opening may be square or rectangular in shape; however, circular, triangular and other geometric and non-geometric shapes are contemplated. In any regard, upon insertion of the second end 38 into the opening 64 a releasable friction fit is formed between an exterior portion of the second end 38 and an interior portion of opening 64. As with other embodiments, the noise suppressor 14, attached via support arm 18, is allowed to rotate between a first position and second position with respect to the base 20.

Figure 10:
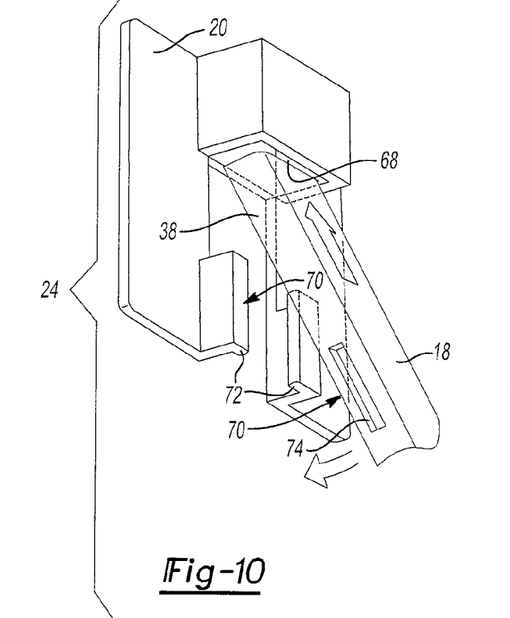
FIG. 10 illustrates a partially exploded perspective view of another exemplary attachment feature according to the teachings of the present invention.

In another exemplary embodiment, referring to FIG. 10, a noise abatement device 10 is provided including an attachment feature 24 that forms an alignment guide and releasable snap-fitting. In this configuration, the base 20 includes an opening 68 configured for receiving the second end 38 of the support arm 18. Once the second end 38 is received within the opening 68, the second end is rotated towards the base 20 to cause engagement between the support arm 18 and base, via releasable snap-fitting 70. The releasable snap-fitting 70 comprises two opposing inwardly facing tabs 72 extending from the base 20, which are configured to engage an interposed arm 74 extending from the support arm 18. During engagement, the inwardly facing tabs 72 elastically deform outward to receive and release the interposed arm 74 thereby forming the releasable snap-fitting.

Figure 11:
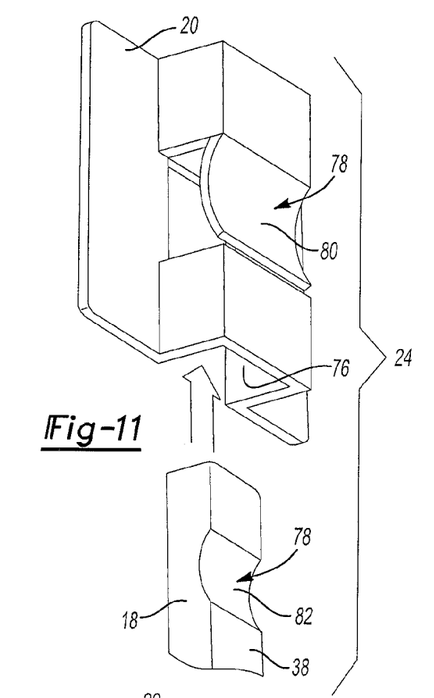
FIG. 11 illustrates a partially exploded perspective view of another exemplary attachment feature according to the teachings of the present invention.

In another exemplary embodiment, referring to FIG. 11, a noise abatement device 10 is provided including an attachment feature 24 that forms an alignment guide and releasable snap-fitting. In this configuration, the base 20 includes an opening 76 configured for receiving the second end 38 of the support arm 18. As the second end 38 is received within the opening 76, a snap-fitting 78 is formed between an inwardly extending tab 80, disposed on the base 20, and a recess 82 formed on the second end 38 of the support arm 18. As the second end 38 of the support arm 18 moves into and out of opening 78, the inwardly extending tab 80 elastically deforms outwardly to receive and release the support arm 18.

In another exemplary embodiment, it is contemplated that the noise suppressor 14 or support arm 18 may be mounted directly to an individual, via a releasable adhesive or other releasable attachment means. This may include attachment to a skin surface of the individual or attachment to clothing, clothing accessories, hardware or otherwise. In one particular exemplary embodiment, a two-sided adhesive tape may be used to mount the second end of the support arm 18 to a skin surface of the individual, wherein flexible resiliency of the skin provides movement of the noise suppressor 14 between a first position and a second position.

Figure 12:
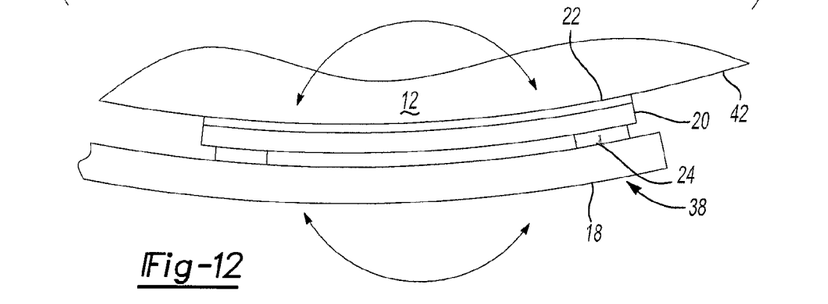
FIG. 12 illustrates an enlarged view of an exemplary connection formed between a noise suppressor and a base according to the teachings of the present invention.
Figure 13:
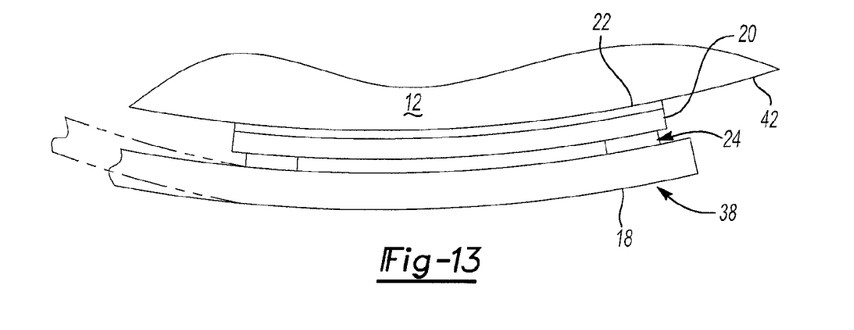
FIG. 13 illustrates an enlarged view of another exemplary connection formed between a noise suppressor and a base according to the teachings of the present invention.
Figure 14:
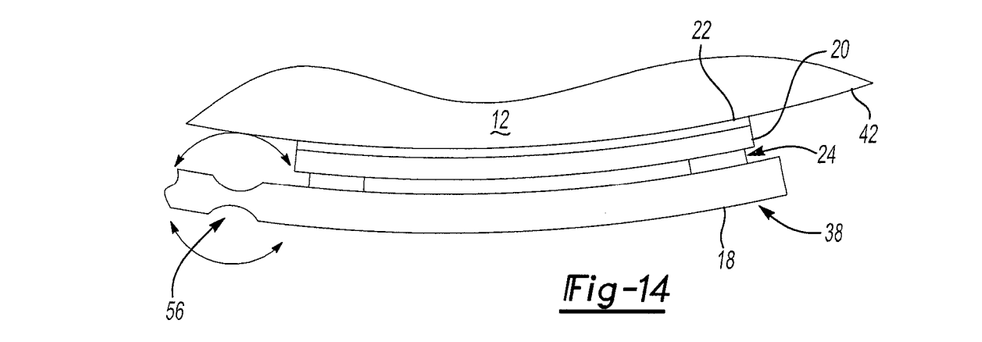
FIG. 14 illustrates an enlarged view of another exemplary connection formed between a noise suppressor and a base according to the teachings of the present invention.
Figure 15:
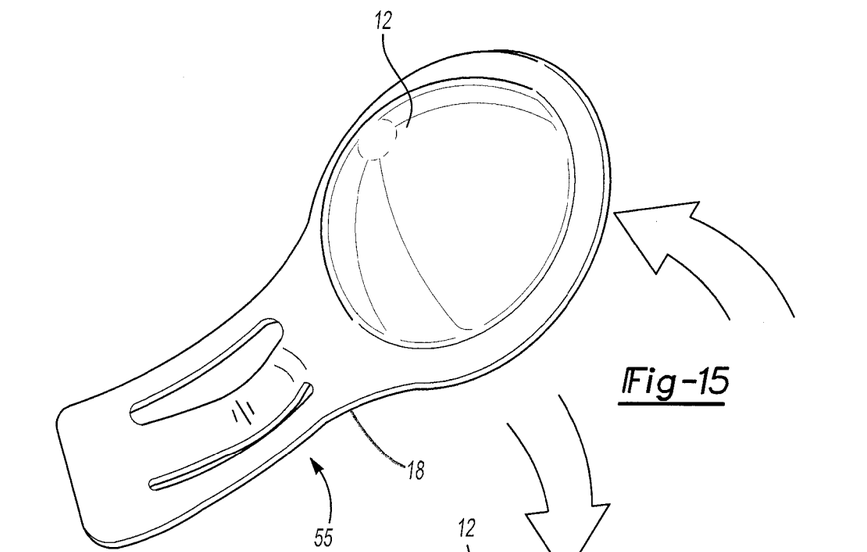
FIG. 15 illustrates a perspective view of another exemplary noise abatement device in a first position according to the teachings of the present invention.
Figure 16:
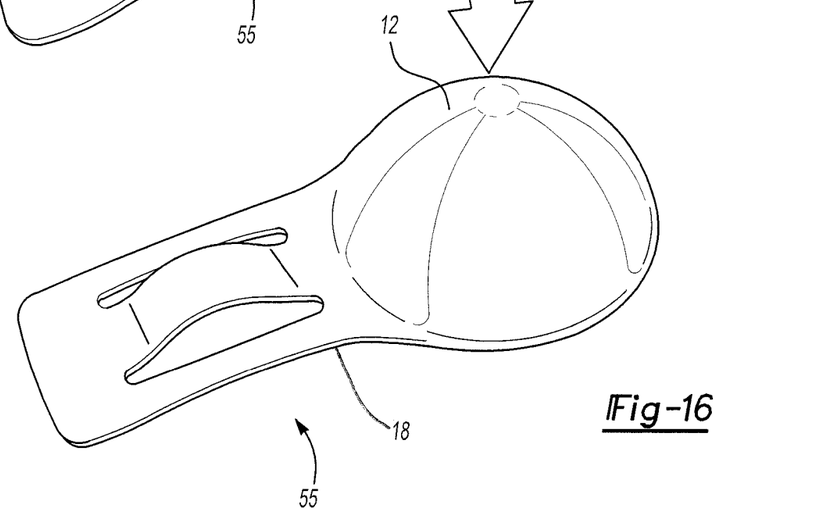
FIG. 16 illustrates a perspective view of another exemplary noise abatement device in a second position according to the teachings of the present invention.
Figure 17:
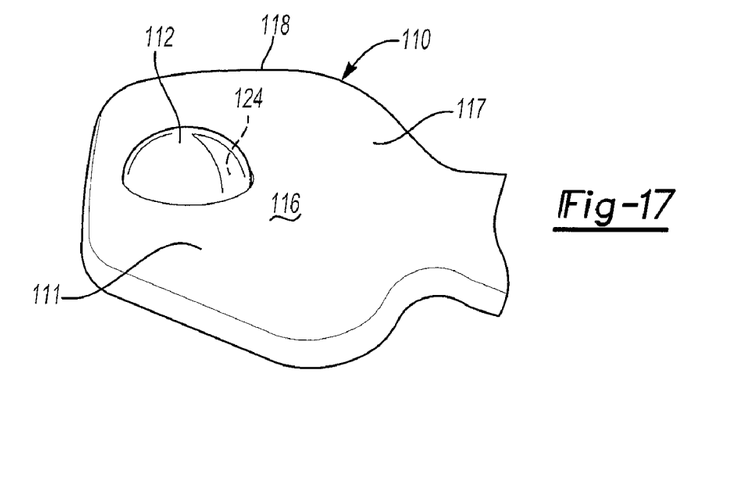
FIG. 17 illustrates a perspective view of an exemplary ostomy bag according to the teachings of the present invention.
Figure 18:
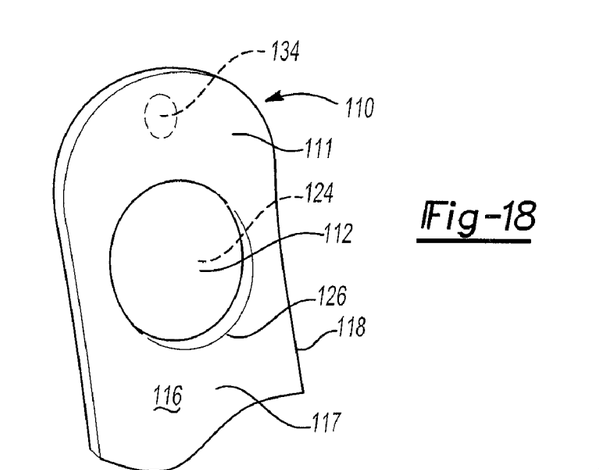
FIG. 18 illustrates a perspective view of a first side of the exemplary ostomy bag shown in FIG. 17.
Figure 19:
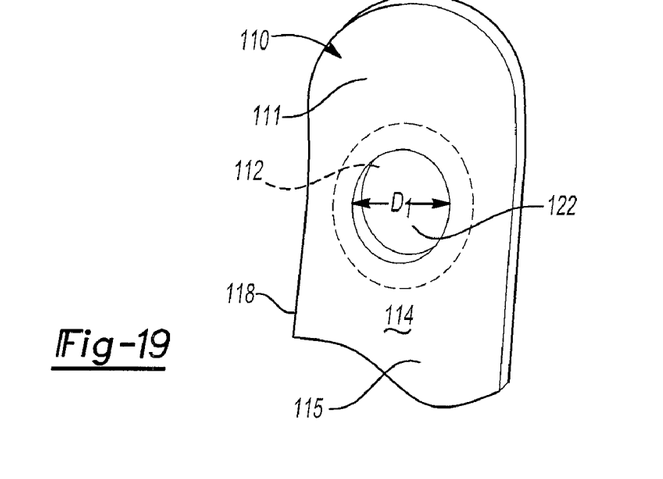
FIG. 19 illustrates a perspective view of a second side of the exemplary ostomy bag shown in FIG. 17.

As previously described, the noise suppressor 14 is configured to move between a first position which is directly adjacent the individual 12 to envelop and seal the stoma 16 from the surrounding area of the individual and a second position wherein the noise suppressor 14 is displaced with respect to the individual. This is particularly advantageous as it reduces the amount of contact between the individual and stoma hardware. In one configuration, the noise suppressor 14 is flexibly attached to the individual 12 through the support arm 18 and base 20. As shown in FIG. 12, this flexible attachment may be achieved through the flexibility of the body wall member 42 of the individual 12. As shown in FIG. 13, the flexibility may be achieved through flexibility of the material forming the noise suppressor 14 and/or support arm 18. In several exemplary embodiments, referring to FIGS. 14 through 16, the noise suppressor 14 includes a hinge, such as spring hinge 55 or living hinge 56, for facilitating movement of the noise suppressor. With particular reference to FIGS. 15 and 16, in one exemplary embodiment, it is contemplated that the spring hinge 55 is configured to maintain the noise suppressor 12 in a first position, second position or both first and second position, wherein when the noise suppressor 12 is moved away from the first or second position, and then released, the noise suppressor returns to its original position. Also, in another configuration, it is contemplated that the spring hinge 55 may be configured to move the noise suppressor 12 to the closer of a first or second position.

The present invention further comprises a method of providing noise abatement for a stoma 16. In one exemplary embodiment, the method comprises pivotally mounting a noise suppressor 14 to an individual 12. In one configuration, the pivotally mounting of the noise suppressor 14 is achieve by mounting a support arm 18, attached to the noise suppressor 14, to a base 20, which is attached to the individual 12 through an epidermis attachment feature 22, such as an adhesive, or otherwise. In one particular configuration, attachment of the support arm 18 to the base 20 is achieved through a releasable attachment feature 24, such as through one or more magnetic attachment members, or otherwise described herein. As described herein, pivotal attachment of the noise suppressor 14 to the individual 12 may be achieved in different manners. In one configuration, the material forming the support arm 16, noise suppressor 14, or both, are flexible and resilient such that the noise suppressor 14 is cantilevered and supported by the base. The noise suppressor is manually pressed against the individual 12, when needed, and upon release returns to a relaxed position, which is displaced with respect to the individual. Accordingly, in a first position, the noise suppressor 14 is pressed against the individual such that the stoma 16 is surrounded and substantially sealed within the cavity 30 of the noise suppressor, via the annular portion 28. Upon release, the noise suppressor 14 moves to a second position that is displaced with respect to the individual 12 to allow movement of the noise suppressor 14 with respect to the individual 12. The return of the noise suppressor 14 may be facilitated, or aided, through elasticity of the body wall member 42 of the individual 12, through flexible resilience of the noise suppressor 14, support arm 18 or both, through hinge 56, combinations thereof or otherwise.

In another exemplary embodiment, the method includes disposing a noise suppressor 14 formed of a closed-cell foam adjacent, and more particularly over, a stoma 16 of an individual 12 such that an opening 29 and a cavity 30 of the noise suppressor is positioned for receiving and enveloping the stoma 16. The method further includes fixedly attaching the noise suppressor 14 to a base 20 that is adhesively attached to an exterior body wall member 42 of the individual 12 to allow the noise suppressor to be manually moved between a first position and a second position. In the first position the noise suppressor 14 is cantilevered and supported by the base member 20, via an integrally formed support arm 18, and is displaced with respect to the individual 12 to allow the noise suppressor 14 to move with respect to the individual and more particularly the stoma 16. In a second position, the noise suppressor 14 is pressed against the individual 12 to envelope the stoma 16 and form a seal about the cavity 30 to seal the stoma 16 from a surrounding area of the individual 12. In one exemplary embodiment, movement of the noise suppressor 14 between the first and second position is facilitated with a hinge 55 or 56, via a living hinge or otherwise. In another exemplary embodiment, movement of the noise suppressor 14 is facilitated through the flexible and resilient support arm 18. In one exemplary embodiment, the noise suppressor 14 is releasably attached to the base 20, such as through a magnetic attachment means, and more particularly through magnetic attachment members 46 disposed on the support arm 18 and base 20, or otherwise as described herein.

In another aspect, the present invention provides an ostomy bag configured for sealing a stoma from a surrounding area for the purpose of sound attenuation. The ostomy bag includes a sound abatement device that is configured to move between a sealed and unsealed position to allow selective sound abatement of the stoma while maintain free flow of waste.

In view of the foregoing, referring to FIGS. 17 through 20, in one exemplary embodiment, the present invention provides an ostomy bag 110 having a sound abatement device 112. The ostomy bag includes a first side 114 formed on a first member 115 and a second side 116 formed on a second member 117. In the configuration shown, the first side is formed of a first substantially water impermeable member 115 and the second side 116 is formed of a second substantially water impermeable member 117, wherein the first and second members are sealed together about a periphery 118 to form a bag 111 and includes a discharge opening 120 for the discharge of accumulated waste.

The first side 114 of the ostomy bag 110 is configured for placement proximate to an individual and more specifically a stoma extending through an abdominal wall lining of the individual. Accordingly, in one exemplary embodiment the first side 114 of the ostomy bag 110 defines an opening 122 for receiving waste expelled from a stoma. The opening includes a diameter '$D_1$' that is suitable in size for receiving the stoma and in certain embodiments for engagement with an attachment feature 128 for attachment of the ostomy bag to an individual. For example, referring to FIG. 20, such attachment feature 124 may comprise an annular ring 130 sized to fit about a stoma 121 and a cylindrical or other shaped member 132 configured to extending around the stoma. The cylindrical member includes an outer diameter and is shaped to correspond to the diameter '$D_1$' and shape of opening 122.

As mentioned above, the ostomy bag 110 includes a sound abatement device 112. In one exemplary embodiment, the sound abatement device is attached to the second surface 116 of the ostomy bag. However, it is also contemplated that the sound abatement device 112 may be integrally formed with the second member 117 forming the second surface. Also, it is contemplated that the sound abatement device 112 may be attached to an interior surface of the second member 117 or otherwise attached to the second member 117. In any regard, attachment of the sound abatement device may be formed through any suitable mean; however, in one exemplary embodiment, the sound abatement device 112 is attached through a water resilient and impermeable adhesive. Other potential attachment means includes hook and latch (e.g. Velcro™), mechanical fasteners (e.g. snap-fitting, threaded fastening or otherwise), magnets or otherwise.

The sound abatement device 112 is positioned and shaped such that upon movement towards and against an abdominal wall 119 of an individual the sound abatement device surrounds a stoma 121 projecting from the abdominal wall and substantially forms a seal between the stoma and surrounding area of the individual. In one exemplary embodiment, the sound abatement device is disposed adjacent the opening formed through the first surface 114 of the ostomy bag 110 and hence the stoma itself.

Figure 20:
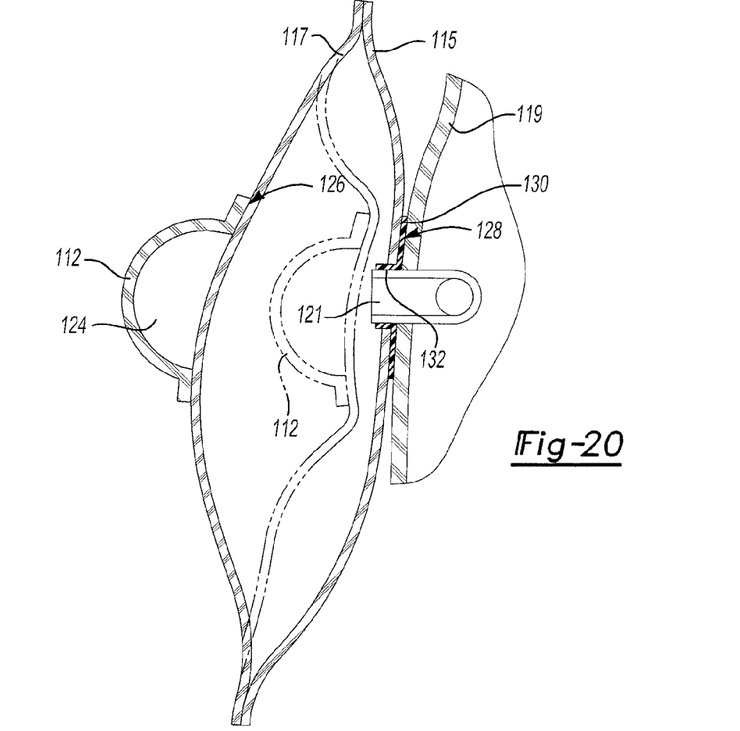
FIG. 20 illustrates a cross-sectional view taken through an exemplary ostomy bag according to the teachings of the present invention.

For example, referring to FIG. 20, the sound abatement device 112 is shaped to receive a stoma 121 and form a substantial seal between the stoma and surrounding area. The sound abatement device 112 includes a cavity 124 for receiving a stoma. In one particular exemplary embodiment, the sound abatement device is semi-spherical, e.g. cup-shaped or otherwise, to form the cavity 124. However, other geometrical and non-geometrical shapes are possible. The cavity is configured with a diameter suitable in shape for receiving the stoma. It is contemplated that the cavity may include a diameter of about or greater than about 2 cm, 3 cm, 4 cm, 5 cm or more. The sound abatement device further includes a seal 126 for causing sealing of the stoma. It should be appreciated that dependent upon forming or attachment of the sound abatement device to the second member 117, the seal may be formed between the sound abatement device 112 and an individual, between the sound abatement device 112 and first member 115 of the ostomy bag 110, between the first member 115 and second member 117 of the ostomy bag or otherwise.

The sound abatement device 112 may be formed of any suitable material for the given application. The sound abatement device may be rigid, semi-rigid and/or flexibly resilient. In one exemplary embodiment, the sound abatement device is formed of a sound dampening material. Examples of suitable materials include rubber, plastic, foam, combinations thereof or otherwise. It is also contemplated that the sound abatement device may include any of the additional sound dampening components described herein such as insert 33 or otherwise. It is also contemplated that the first or second member 115, 117, may also be formed of a sound dampening material, including any of the materials described with the sound abatement device 112. In one exemplary embodiment, the ostomy bag 110 may further include a vent 134 for selective release of gas trapped within the ostomy bag.

In one exemplary mode of operation, referring again to FIG. 20, the ostomy bag 110 of the present invention is attached to an abdominal wall 119 of an individual, through attachment feature 128 or otherwise. Upon attachment, the stoma 121 of the individual extends through the opening 122 defined by the second side 116 of the second member 115 and the sound abatement device 112 is adjacently disposed with respect to the stoma to allow waste to freely enter the bag 111. Once the individual anticipates the expulsion of gas through the stoma 121, he or she presses the sound abatement device 112 against the abdominal wall 119 to form a seal between the stoma and surrounding area. Upon release, the sound abatement device 112 returns to a position disposed with respect to the stoma 121. Gas may be selectively released from within the bag 111 through vent 134. It should be appreciated that more or less steps may be included with the above exemplary mode of operation as shown or described herein, or otherwise.

Figure 21:
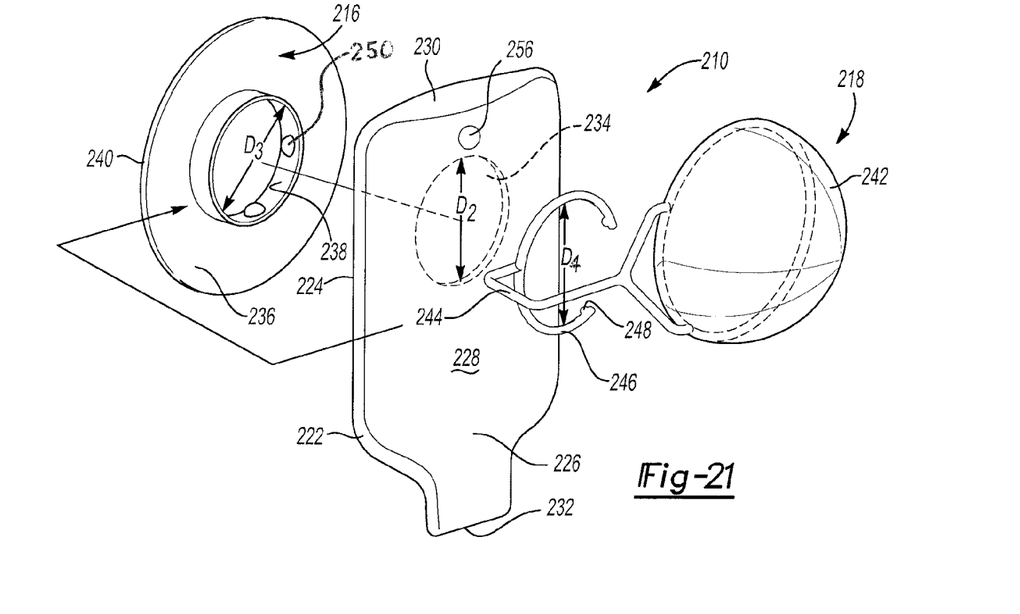
FIG. 21 illustrates an exploded perspective view of an exemplary ostomy device according to the teachings of the present invention.
Figures 22, 23:
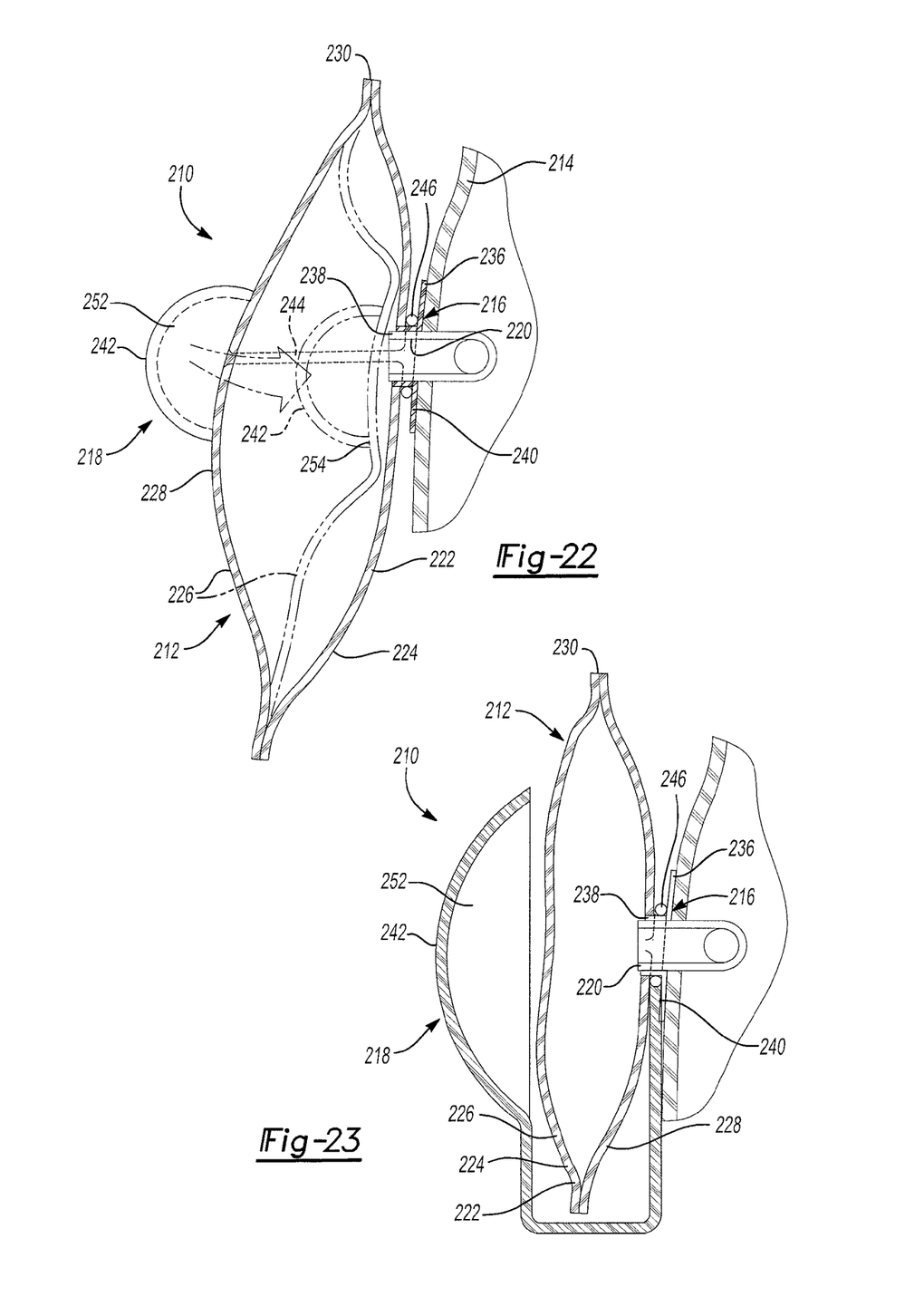
FIG. 22 illustrates a side cross-sectional view of the ostomy device shown in FIG. 21.
FIG. 23 illustrates a top cross-sectional view of the ostomy device shown in FIG. 21.

In another aspect, referring to FIGS. 21 through 23, the present invention provides an ostomy device 210 configured for the collection of waste from a stoma and sound abatement thereto. The ostomy device 210 includes a bag 212 configured for attachment to an abdominal wall 214 of an individual through a mount 216. The ostomy device 210 further includes a sound abatement device 218 configured for attachment to the mount 216 and provides selective sealing of a stoma 220 from a surrounding area of the individual 214. The sound abatement device 218 is moveable with respect to the stoma to provide selective sealing of the stoma 220 in a first position and displacement from the individual 214 in a second position to reduce irritation.

In greater detail, the bag 212 includes a first member 222 having a first side 224 and a second member 226 having a second side 228. The first and second members 222, 226 are sealed about a periphery 230 to form a bag including a discharge opening 232 for emptying excrement from within the bag. The first member 222 defines an opening 234 for receiving excrement from the stoma 220. The first member 222 is also configured for attachment of the bag 212 to the mount 216. In one exemplary embodiment, the opening 234 includes a diameter 'D₂' that is greater than a stoma 220 for allowing the stoma to extend through the opening. Also, in one exemplary embodiment, the diameter 'D₂' is shaped and size to engage the mount 216.

The mount 216 is configured for attachment to an individual to provide protection to the stoma 220 and attachment of the bag 212 to the abdominal wall 214 of an individual. In one exemplary embodiment, the mount 216 includes an annular ring 236 and a projecting member 238 extending from the annular ring. The annular ring 236 includes an attachment surface 240 for attachment to the abdominal wall 214. In one exemplary embodiment, the mount includes adhesive or other attachment means dispose on or proximate attachment surface 240 for attachment to the abdominal wall 214. The projecting member 238 is sized and shaped to provide protection to the stoma 220 extending from the abdominal wall 214. In one exemplary embodiment, the projecting member is cylindrical in shape and includes a diameter 'D₃' corresponding to the diameter 'D₂' of opening 234 of the bag 212.

As mentioned above, the ostomy device 210 includes a sound abatement device 212 that is configured for attached to the mount 216. In one exemplary embodiment, the sound abatement device 218 includes sound suppressor 242 connected to the mount 216 through an arm 244 and a connector 246. The arm 244 is shaped to extend generally about the bag 212 so as to prevent deformation of the bag during movement of the sound suppressor 242. The connector 246 is shaped and sized to provide releasable engagement with the mount 216. In one exemplary embodiment, the connector comprises a c-shaped connector having a diameter 'D₄' configured for snap-fit engagement with the projecting member 238. In one exemplary embodiment, the connector 246 includes tabs 248 or other features configured to engage recesses 250 formed in the projecting member 238 to prevent rotation of the sound abatement device 212. However, the connector 246 may be shaped for other attachment configurations such as friction fit or otherwise.

The sound suppressor 242 is positioned and shaped such that upon movement towards and against an abdominal wall 214 of an individual the sound abatement device surrounds a stoma 220 projecting from the abdominal wall and substantially forms a seal between the stoma and surrounding area of the individual. In one exemplary embodiment, the sound abatement device is disposed adjacent the opening 234 formed through the first surface 224 of the bag 212 and hence the stoma 220 itself.

For example, referring to FIGS. 22 and 23, the sound suppressor 242 is shaped to receive a stoma 220 and form a substantial seal between the stoma and surrounding area. In one exemplary embodiment, the sound suppressor 242 includes a cavity 252 for receiving a stoma. In one particular exemplary embodiment, the sound abatement device is semispherical, e.g. cup-shaped or otherwise, to form the cavity 252. However, other geometrical and non-geometrical shapes are possible. The cavity is configured with a diameter suitable in shape and size for receiving the stoma. It is contemplated that the cavity may include a diameter of about or greater than about 2 cm, 3 cm, 4 cm, 5 cm or more. The sound abatement device further includes a seal 254 for causing sealing of the stoma 220.

The sound suppressor 242 may be formed of any suitable material for the given application. In exemplary embodiments, the sound suppressor 242 is rigid, semi-rigid and/or flexibly resilient. In one exemplary embodiment, the sound suppressor 242 is formed of a sound dampening material. Examples of suitable materials include rubber, plastic, foam, combinations thereof or otherwise. It is also contemplated that the sound abatement device may include any of the additional sound dampening components described herein such as insert 33 or otherwise. It is also contemplated that the arm 244 or connector 246 may be formed of a rigid or semi-rigid and flexible resilient material and may be formed of the same material forming the sound suppressor 242. Accordingly, the sound suppressor 242, arm 244 and connector 246 may be integrally formed of the same material or may be separately formed and attached together.

In one exemplary embodiment, the bag 212 further include a vent 256 for selective release of gas trapped within the bag. In this embodiment, it is contemplated that the sound suppressor 242 may be sized and shaped to cover and seal the vent 256 from the surrounding area of the individual.

In one exemplary mode of operation, referring to FIG. 22, the bag 212 of the present invention is attached to an abdominal wall 214 of an individual, through mount 216. Upon attachment, the stoma 220 of the individual extends through the opening 234 defined by the second side 228 of the second member 226. The sound abatement device 218 is attached to the mount 216 and positioned such that the sound suppressor 242 is adjacently disposed with respect to the stoma 220. Once the individual anticipates the expulsion of gas through the stoma 220, he or she presses the sound suppressor 242 against the abdominal wall 214 to form a seal between the stoma and surrounding area. Upon release, the sound suppressor 242 returns to a position disposed with respect to the stoma 220 through the resiliency of arm 244 of the sound abatement device 218. Gas may be selectively released from within the bag 212 through vent 256. It should be appreciated that more or less steps may be included with the above exemplary mode of operation as shown or described herein.

While the invention has been described with reference to a preferred embodiment it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A sound abatement device for an abdominal stoma, the device comprising:
   a noise suppressor formed of sound dampening material, the noise suppressor defines an opening and cavity suitable in size and shape for receiving and enveloping a stoma formed through a body wall of an individual;
   a support arm extending laterally away from the noise suppressor, the support arm includes a first end connected to the noise suppressor and a second end disposed opposite thereof;
   a base member disposed proximate the second end of the support arm and remote from the noise suppressor, the base member includes an attachment for connection to an individual; and
   an attachment feature for releasable attachment of the second end of the support arm to the base, wherein upon engagement the noise suppressor is cantilevered from the base.

2. The device of claim 1, wherein the sound dampening material comprises closed-cell foam.

3. The device of claim 1, wherein the noise suppressor includes an annular seal formed about the opening.

4. The device of claim 1, wherein the support arm is formed of a resilient flexible material to provide for movement of the noise suppressor with respect to the base member.

5. The device of claim 1, further comprising a hinge formed between the noise suppressor and base member for movement of the noise suppressor with respect to the base member.

6. The device of claim 1, wherein the support arm is integrally formed with the noise suppressor.

7. The device of claim 1, further comprising an adhesive suitable for adhesive bonding of the base member to a skin surface of an individual.

8. The device of claim 1, wherein the attachment feature magnetically attaches the support arm to the base.

9. The device of claim 1, wherein the attachment feature comprises a hook and latch, snap-fitting, threaded fastener, magnets or combinations thereof.

10. The device of claim 1, wherein the support arm includes a hinge for movement of the noise suppressor between a first position and a second position.

11. The device of claim 1, further comprising a belt configured for wrapping about an individual, the base being attached to the belt through the attachment.

12. A method of providing noise abatement for a surgically created abdominal stoma utilizing the sound abatement device of claim 1, the method comprising the steps of:
pivotally mounting a noise suppressor to an individual, the noise suppressor being moveable between a first position and a second position, wherein in the first position the noise suppressor envelops a stoma and substantially seals the stoma from a surrounding area of the individual, and wherein in a second position the noise suppressor is spaced from the individual.

13. The method of claim 12, wherein the noise suppressor is releasably attached to the individual.

14. The method of claim 13, wherein attachment of the noise suppressor to the individual is achieved through magnetic attachment of the noise suppressor to a base member.

15. The method of claim 12, further comprising a hinge for facilitating movement of the noise suppressor with respect to the stoma.

16. The method of claim 12, wherein the noise suppressor is formed of a resilient flexible material.

17. The method of claim 16, wherein the material forming the noise suppressor comprises closed-cell foam.

18. The method of claim 12, wherein the noise suppressor is manually moveable towards the first position and upon release the noise suppressor returns to the second position.

19. A sound abatement device for an abdominal stoma, the device comprising:
a noise suppressor
defining an opening and cavity suitable in size and shape for receiving and enveloping a stoma formed through a body wall of an individual,
the noise suppressor includes an integrally formed support arm extending laterally away from the noise suppressor,
wherein the noise suppressor defines a seal formed about the cavity configured to engage a body wall of an individual;
a base member disposed proximate an end of the support arm opposite the opening and cavity and remote from the noise suppressor, the base member includes a first side and an attachment for connection to a body wall of an individual and a second side configured for connection to the noise suppressor; and
an attachment feature for releasable attachment of the second end of the support arm to the second side of the base member,
wherein upon attachment of the support arm to the base member the noise suppressor is moveable from a first position to a second position.

20. The device of claim 19, further comprising a belt configured for wrapping about an individual, the first surface of the base being attached to the belt through fasteners.

\* \* \* \* \*